(12) United States Patent
Pustilnik et al.

(10) Patent No.: US 9,931,445 B2
(45) Date of Patent: Apr. 3, 2018

(54) SYSTEM AND METHODS FOR PREPARATION OF ADIPOSE-DERIVED STEM CELLS

(75) Inventors: Felix Pustilnik, Walnut Creek, CA (US); Nathan Katz, Mount Prospect, IL (US)

(73) Assignee: JOINTECHLABS, INC., Mount Prospect, IL (US)

( * ) Notice: Subject to any disclaimer, the term of this patent is extended or adjusted under 35 U.S.C. 154(b) by 0 days.

(21) Appl. No.: 13/544,909

(22) Filed: Jul. 9, 2012

(65) Prior Publication Data

US 2013/0012921 A1    Jan. 10, 2013

Related U.S. Application Data

(60) Provisional application No. 61/505,936, filed on Jul. 8, 2011.

(51) Int. Cl.
| | | |
|---|---|---|
| *A61M 1/00* | (2006.01) | |
| *B01L 3/00* | (2006.01) | |
| *A61K 35/28* | (2015.01) | |
| *C12N 5/0775* | (2010.01) | |
| *A61M 1/36* | (2006.01) | |

(52) U.S. Cl.
CPC ............ *A61M 1/00* (2013.01); *A61K 35/28* (2013.01); *B01L 3/5021* (2013.01); *B01L 3/50825* (2013.01); *C12N 5/0667* (2013.01); *A61M 1/3693* (2013.01); *A61M 2202/08* (2013.01); *B01L 2300/0867* (2013.01); *B01L 2400/0409* (2013.01)

(58) Field of Classification Search
CPC .. A61M 1/00; A61M 1/3693; A61M 2202/08; A61K 35/28; B01L 2300/0867; B01L 2400/0409; B01L 3/5021; B01L 3/50825; C12N 5/0667
USPC ............................ 604/92, 518; 435/325, 374
See application file for complete search history.

(56) References Cited

U.S. PATENT DOCUMENTS

| | | | |
|---|---|---|---|
| 2005/0076396 A1* | 4/2005 | Katz et al. .................. | 800/8 |
| 2010/0317099 A1 | 12/2010 | Leach et al. | |
| 2011/0117650 A1 | 5/2011 | Riordan | |
| 2011/0251041 A1* | 10/2011 | Chavarria et al. ............ | 494/4 |

FOREIGN PATENT DOCUMENTS

| | | |
|---|---|---|
| EP | 1921133 A2 | 5/2008 |
| JP | 2012-035004 A | 2/2012 |
| WO | 2012/006587 A2 | 1/2012 |
| WO | 2012/083260 A2 | 6/2012 |

OTHER PUBLICATIONS

International Search Report and Written Opinion for Int. App. No. PCT/US2013/025465, dated May 30, 2013.
European Search Report for EP Application No. 13816214.4, dated Jun. 27, 2016.

* cited by examiner

*Primary Examiner* — Janet L Epps-Smith
(74) *Attorney, Agent, or Firm* — McDonnell Boehnen Hulbert & Berghoff LLP

(57) ABSTRACT

A system for extracting and processing adipose tissue to generate a therapeutically effective amount of adipose-derived stem cells, comprising an adipose tissue extraction device and a modified centrifuge tube comprising a plurality of lipoaspirate inlet fittings, a plurality of processing fluid inlet fittings, and a plurality of pellet extraction tubes. The adipose tissue extraction device is used to extract a quantity of adipose tissue from a human being, the lipoaspirate is moved into the first modified centrifuge tube via a sterile transfer, a plurality of processing steps are performed to clean and dissociate the lipoaspirate, and a pellet containing an enhanced fraction of stem cells is obtained by centrifuging the modified centrifugal tube. The pellet is resuspended in a fluid and administered to a human patient for a therapeutic or cosmetic purpose.

17 Claims, 5 Drawing Sheets

SYSTEM AND METHODS FOR PREPARATION OF ADIPOSE-DERIVED STEM CELLS

RELATED APPLICATIONS

This application claims priority to U.S. provisional patent application Ser. No. 61/505,936, titled "KIT FOR THE PREPARATION OF ADIPOSE-DERIVED STEM CELLS", filed on Jul. 8, 2011, the entire specification of which is incorporated herein by reference.

BACKGROUND OF THE INVENTION

1. Field of the Invention

This invention generally systems for preparing and using stems cells derived from adipose tissue, adipose-derived stem cells obtained with such kit, methods of using such adipose-derived stem cells, compositions containing such adipose-derived stem cells.

2. Discussion of the State of the Art

Regenerative medicine can be defined as harnessing the body's regenerative mechanisms in a clinically targeted manner, using them in ways that are not part of the normal healing mechanism or by artificially amplifying normal mechanisms. One classic example of this process is found in bone marrow transplantation where hematopoietic stem and progenitor cells are harvested from a donor and placed into a recipient, in whom the normal hematopoietic regenerative mechanisms have been ablated or substantially depleted or impaired, thereby replacing or regenerating the blood-forming capacity of the recipient. This approach has been extended to the non-hematopoietic stem cells from a variety of sources for multiple therapeutic or prophylactic purposes. In particular, it has been demonstrated that adipose tissue can readily be used as a source of multipotent mesenchymal stem cells suitable for therapeutic or prophylactic use.

Mesenchymal Stem Cells ("MSCs") are pluripotent stem cells that can differentiate readily into lineages including osteoblasts, myocytes, chondrocytes, adipocytes, endothelial cells, and beta pancreatic islet cells (Pittenger, et al., Science, Vol. 284, pg. 143 (1999); Haynesworth, et al., Bone, Vol. 13, pg. 69 (1992); Prockop, Science, Vol. 276, pg. 71 (1997)). MSCs, also known in the literature as bone marrow stem cells, skeletal stem cells, and multipotent mesenchymal stromal cells, are non-hematopoietic progenitor cells isolated from adult tissues, and are characterized in vitro by their extensive proliferative ability in an uncommitted state while retaining the potential to differentiate along various lineages of mesenchymal origin, including chondrocyte, osteoblast, and adipocyte lineages, in response to appropriate stimuli. In vitro studies have demonstrated the capability of MSCs to differentiate into muscle (Wakitani, et al., Muscle Nerve, Vol. 18, pg. 1417 (1995)), neuronal-like precursors (Woodbury, et al., J. Neurosci. Res., Vol. 69, pg. 908 (2002); Sanchez-Ramos, et al., Exp. Neurol., Vol. 171, pg. 109 (2001)), cardiomyocytes (Toma, et al., Circulation, Vol. 105, pg. 93 (2002); Fakuda, Artif. Organs, Vol. 25, pg. 187 (2001)) and possibly other cell types. MSCs are present in multiple tissues in the body, which arise from the embryonic mesoderm (e.g., hematopoietic cells and connective tissue). As such, pluripotent cells can be isolated from any of these tissue sources and can be induced to differentiate into any of these cell types.

A convenient source of adipose tissue is from liposuction surgery. In fact, a large quantity of pluripotent cells can be obtained by simple aspiration from adipose tissue, for example, from lipoaspirate samples from aesthetic interventions. The present invention is directed in particular to a system for isolating MSCs from adipose tissue. As used herein, "adipose tissue" refers to a tissue containing multiple cell types including adipocytes and microvascular cells. Adipose tissue includes stem cells and endothelial precursor cells. Accordingly, adipose tissue refers to fat including the connective tissue that stores the fat.

It has been discovered that adipose tissue is an especially rich source of stem cells. This finding may be due, at least in part, to the ease of removal of the major non-stem cell component of adipose tissue, the adipocyte. However, processing of adipose tissues to separate pluripotent cells and expansion and (optionally) differentiation of the resulting stem cell population, according to systems and methods known in the art, generally requires expensive, specialized equipment and equally expensive, specialized processes. The costs associated with purpose-built devices for repeated stem cell extraction from adipose tissues obtained by, for example, liposuction from a living human donor have restricted the use of stem cell-rich media for therapeutic purposes to large hospitals and research facilities. As a result, use of adipose-derived stem cell-based therapies by small physician or other professional practices has not been possible or economical. Moreover, use of stem cell-based cosmetic enhancement techniques has been hampered by the high cost and low availability of systems and methods currently in the art for extracting and culturing stem cells derived from adipose tissues.

What is needed are techniques and systems that facilitate economical and safe extraction of therapeutically or cosmetically useful quantities of adipose-derived stem cells, whether in pure form or as part of a stem cell enriched medium, and specifically techniques and systems that are suitable for use in small professional practices without requiring capital investments of specialized facilities.

SUMMARY OF THE INVENTION

The inventor has conceived, and reduced to practice, a system and various methods for preparation of adipose-derived stem cells that addresses the challenges and problems in the art outlined above. A cell population from human adipose tissue may be used as a source of cells for therapeutic and cosmetic applications. Among other things, adipose-derived stem cells, either in pure form (stem cells only) or in enriched form (cell cultures with an augmented fraction of stem cells relative to those occurring in vivo in adipose tissues) may be used for regenerative medicine, such as treatment of diseases that may be ameliorated or cured through use of regenerating cells. Cells of a prepared population may be administered to a patient without other adipocytes or connective tissue, or may be administered mixed together with adipose tissue in a concentrated amount, as discussed herein. The present invention is directed to a system for obtaining a purified fraction of adipose-derived mesenchymal stem cells from adipose tissue and administering the purified fraction back into a human or animal patient. The present invention provides a system for extracting adipose tissue (lipoaspirate) and processing it to generate a processed lipoaspirate (PLA) which contains stem cells at a frequency of at least 0.1%, and more typically greater than 0.5%. PLA can in some embodiments be obtained comprising between about 2-12% stem cells, and PLA with up to 100% of cells in a population comprised of stem cells are possible, according to the invention.

The present invention is directed to a system for obtaining a substantially purified or enriched fraction of adipose-derived mesenchymal stem cells in a clinical environment and also to compositions, methods, and systems for using stem cells derived from adipose tissue that are placed directly into a recipient along with such additives as may be necessary to promote, engender, or support a therapeutic, structural, or cosmetic benefit. Embodiments of the invention provide a multi-component system for extracting and processing adipose tissue to generate a therapeutically effective amount of adipose-derived stem cells for re-introduction into a patient. Advantageously, the system does not require full operating room environment or full-scale lipoaspiration and can therefore be operated outside of a hospital or laboratory environment. The system is therefore suitable for small and mid-size medical clinics, outpatient surgical centers, and doctor's offices of multidisciplinary specialization.

In an embodiment, a system, called the Mini-Stem™ system, allows for small physician practices as well as surgical centers to employ affordable methods for safe extraction of MSC from adipose tissue of any patient for treatment or cryostorage (banking). The system comprises means for carrying out a secure, sterile, and closed process in which a small sample of fat is extracted (for example, by liposuction) as a lipoaspirate; materials for on-site processing and purification of MSC fractions; and optionally tools to assist in quality assessment of resulting processed lipoaspirate. The system is operable by a lab technician following simple method steps taught in appropriate training.

In an embodiment, adipose tissue processing occurs in a system that maintains a closed, sterile fluid/tissue pathway. This is achieved by use of a kit of sterile containers and tubing that allows for transfer of tissue and fluid elements within a closed pathway. A series of processing reagents (e.g., saline, enzymes, etc.) are also provided prepackaged for introduction into the sterile containers to allow simple control of the addition of reagents, temperature, and timing of processing thus simplify the process by which operators manually manage the process. In a preferred embodiment the entire procedure from tissue extraction through processing and placement into the recipient would all be performed in the same facility, indeed, even within the same room of the patient undergoing a procedure according to the invention.

In accordance with one aspect of the invention, a small amount of raw adipose tissue is extracted from a patient into a sterile container of the kit. The raw adipose tissue is processed within one or more sterile containers of the kit to substantially remove mature adipocytes and connective tissue, thereby obtaining a heterogeneous plurality of adipose tissue-derived cells suitable for placement within the body of a recipient. Reagents needed for processing of adipose tissue are provided as part of the kit and introduced to the one or more sterile containers according to a predetermined schedule to generate a processed lipoaspirate including a desired concentration of adipose-derived stem cells. The adipose-derived stem cells, or a modified lipoaspirate that is enriched with a higher stem cell fraction than occurs in vivo, may then be placed into a recipient in combination with other cells, tissue, tissue fragments, or other stimulators of cell growth and/or differentiation. In a preferred embodiment, stem cells, with any of the above-mentioned additives, are placed into a person from whom they were obtained in the context of a single operative procedure with the intention of deriving a therapeutic, structural, or cosmetic benefit to the recipient.

In an embodiment of the invention, a method of treating a patient includes steps of: a) providing a disposable tissue removal system as a component of the kit; b) removing adipose tissue from a patient using the disposable tissue removal system, the adipose tissue having a concentration of stem cells; c) processing within one or more sterile containers of the kit at least a part of the adipose tissue to obtain a concentration of stem cells higher than the concentration of stem cells of the adipose tissue before processing; and d) administering the stem cells to a patient from a sterile container of the kit.

In a preferred embodiment of the invention, a system for extracting and processing adipose tissue to generate a therapeutically effective amount of adipose-derived stem cells, comprising an adipose tissue extraction device and a modified centrifuge tube comprising a plurality of lipoaspirate inlet fittings, a plurality of processing fluid inlet fittings, and a plurality of pellet extraction tubes. The adipose tissue extraction device is used to extract a quantity of adipose tissue from a human being, the lipoaspirate is moved into the first modified centrifuge tube via a sterile transfer, a plurality of processing steps are performed to clean and dissociate the lipoaspirate, and a pellet containing an enhanced fraction of stem cells is obtained by centrifuging the modified centrifugal tube. The pellet is resuspended in a fluid and administered to a human patient for a therapeutic or cosmetic purpose. According to another embodiment, the system further comprises a second modified centrifuge tube of a substantially similar design as the first modified centrifuge tube, wherein the second modified centrifuge tube is used to further process the resuspended pellet to achieve a higher concentration of stem cells.

According to another preferred embodiment of the invention, a method for preparation of adipose-derived stem cells, the method comprising the steps of: (a) removing adipose tissue from a human being using an adipose tissue extraction device; (b) performing a sterile transfer of the lipoaspirate to a modified centrifuge tube comprising a plurality of lipoaspirate inlet fittings, a plurality of processing fluid inlet fittings, and a plurality of pellet extraction tubes; (c) processing the lipoaspirate in the modified centrifuge tube by adding one or more fluids via the plurality of processing fluid fittings, the processing comprising one or more of cleaning and dissociating the lipoaspirate; (d) centrifuging the modified centrifuge tube containing processed lipoaspirate to concentrate a pellet comprising an enriched stem cell fraction; (e) resuspending the pellet in a fluid to obtain a cell mixture substantially enriched in stem cells relative to a concentration of stem cells of the original lipoaspirate; and (f) administering the resuspended cell mixture to a human being for a therapeutic or cosmetic purpose.

These and other objects, features and advantages of the invention will be apparent from the detailed description that follows.

BRIEF DESCRIPTION OF THE DRAWING FIGURES

The accompanying drawings illustrate several embodiments of the invention and, together with the description, serve to explain the principles of the invention according to the embodiments. One skilled in the art will recognize that the particular embodiments illustrated in the drawings are merely exemplary, and are not intended to limit the scope of the present invention.

DETAILED DESCRIPTION

Figure 1:
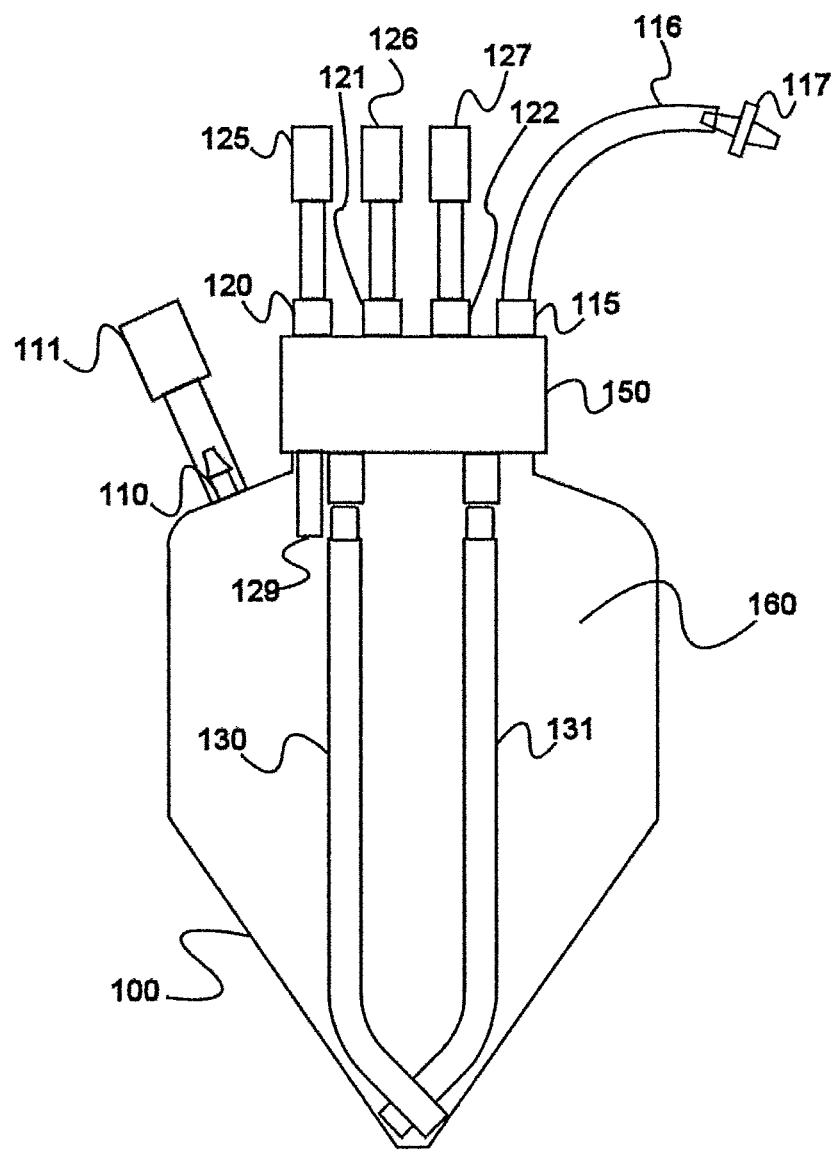
FIG. 1 is a diagram illustrating a modified centrifuge tube for extracting stem cells from adipose tissue, according to a preferred embodiment of the invention.

The inventor has conceived, and reduced to practice, a system and various methods for preparation of adipose-derived stem cells that addresses the challenges and problems in the art outlined above. Various techniques will now be described in detail with reference to a few example embodiments thereof, as illustrated in the accompanying drawings. In the following description, numerous specific details are set forth in order to provide a thorough understanding of one or more aspects and/or features described or referenced herein. However, it will be apparent to one skilled in the art, that one or more aspects and/or features described or referenced herein may be practiced without some or all of these specific details. In other instances, well known process steps and/or structures have not been described in detail in order to not obscure some of the aspects and/or features described or reference herein.

One or more different inventions may be described in the present application. Further, for one or more of the inventions described herein, numerous alternative embodiments may be described; it should be understood that these are presented for illustrative purposes only. The described embodiments are not intended to be limiting in any sense. One or more of the inventions may be widely applicable to numerous embodiments, as is readily apparent from the disclosure. In general, embodiments are described in sufficient detail to enable those skilled in the art to practice one or more of the inventions, and it is to be understood that other embodiments may be utilized and that structural, logical, software, electrical and other changes may be made without departing from the scope of the particular inventions. Accordingly, those skilled in the art will recognize that one or more of the inventions may be practiced with various modifications and alterations. Particular features of one or more of the inventions may be described with reference to one or more particular embodiments or figures that form a part of the present disclosure, and in which are shown, by way of illustration, specific embodiments of one or more of the inventions. It should be understood, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only, and are not to be taken as limiting the disclosure in any way.

A description of an embodiment with several components in communication with each other does not imply that all such components are required. To the contrary, a variety of optional components may be described to illustrate a wide variety of possible embodiments of one or more of the inventions and in order to more fully illustrate one or more aspects of the inventions. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the invention(s), and does not imply that the illustrated process is preferred. Also, steps are generally described once per embodiment, but this does not mean they must occur once, or that they may only occur once each time a process, method, or algorithm is carried out or executed. Some steps may be omitted in some embodiments or some occurrences, or some steps may be executed more than once in a given embodiment or occurrence.

When a single device or article is described, it will be readily apparent that more than one device or article may be used in place of a single device or article. Similarly, where more than one device or article is described, it will be readily apparent that a single device or article may be used in place of the more than one device or article.

The functionality or the features of a device may be alternatively embodied by one or more other devices that are not explicitly described as having such functionality or features. Thus, other embodiments of one or more of the inventions need not include the device itself.

Techniques and mechanisms described or referenced herein will sometimes be described in singular form for clarity. However, it should be noted that particular embodiments include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of embodiments of the present invention in which, for example, functions may be executed out of order from that shown or discussed, including substantially concurrently or in reverse order, depending on the functionality involved, as would be understood by those having ordinary skill in the art.

Any feature or combination of features described herein are included within the scope of the present invention provided that the features included in any such combination are not mutually inconsistent as will be apparent from the context, this specification, and the knowledge of one of ordinary skill in the art. For purposes of summarizing the present invention, certain aspects, advantages and novel features of the present invention have been described herein. Of course, it is to be understood that not necessarily all such aspects, advantages, or features will be embodied in any particular embodiment of the present invention. Additional advantages and aspects of the present invention are apparent in the following detailed description and claims.

A number of publications and patents have been cited herein. Each of the cited publications and patents is hereby incorporated by reference in their entireties. All publications, patents, and patent applications referenced herein are incorporated by reference in their entirety to the same extent as if each individual publication, patent or patent application was specifically and individually indicated as incorporated by reference in its entirety.

Definitions

As used herein, "unit of adipose tissue" refers to a discrete or measurable amount of adipose tissue. A unit of adipose tissue may be measured by determining the weight and/or volume of the unit. Based on the data identified above, a unit of processed lipoaspirate, as removed from a patient, has a cellular component in which at least 0.1% of the cellular component is stem cells. In reference to the disclosure herein, a unit of adipose tissue may refer to the entire amount of adipose tissue removed from a patient, or an amount that is less than the entire amount of adipose tissue removed from a patient. Thus, a unit of adipose tissue may be combined with another unit of adipose tissue to form a unit of adipose tissue that has a weight or volume that is the sum of the individual units.

As used herein, "portion" refers to an amount of a material that is less than a whole. A minor portion refers to an amount that is less than 50%, and a major portion refers to an amount greater than 50%. Thus, a unit of adipose tissue that is less than the entire amount of adipose tissue removed from a patient is a portion of the removed adipose tissue.

As used herein, "stem cell" refers to a multipotent cell with the potential to differentiate into a variety of other cell types, which perform one or more specific functions and have the ability to self-renew. Some of the stem cells disclosed herein may be pluripotent.

As used herein, "processed lipoaspirate" (PLA) refers to adipose tissue that has been processed to separate the active cellular component (e.g., the component containing stem cells) from the mature adipocytes and connective tissue. Typically, PLA refers to the pellet of cells obtained by washing and separating the cells from the adipose tissue. The pellet is typically obtained by centrifuging a suspension of cells so that the cells aggregate at the bottom of a centrifuge container.

As used herein the term "prophylactically or therapeutically effective amount" refers to the amount of cells of the invention contained in the pharmaceutical composition that is capable of producing the desired therapeutic effect. One of skill in the art will recognize that cell numbers (e.g., dosage amount) will vary depending upon multiple factors including, but not limited to site of administration, extent of disease, and method of administration. Experience with transplant of hematopoietic stem cells (bone marrow or umbilical cord blood-derived stem cells used to regenerate the recipient's blood cell-forming capacity) shows that engraftment is cell dose-dependent with threshold effects. Thus, it is likely that the general principle that "more is better" will be applied within the limits set by other variables and that where feasible the harvest will collect as much tissue as possible. The dose of cells disclosed herein can be repeated, depending on the patient's condition and reaction, at time intervals of days, weeks or months as determined necessary by a treating physician or other healthcare professional.

The term "pharmaceutically acceptable vehicle" refers to a composition approved by a regulatory agency of the Federal or a state government or listed in the U.S. Pharmacopeia, or European Pharmacopeia or other generally recognized pharmacopeia for use in animals, including humans. The term "vehicle" refers to a diluent, adjuvant, excipient, or carrier with which the cells of the invention are administered, thus, the vehicle must be compatible with the cells. The pharmaceutical compositions of the invention, if desired, can also contain, when necessary, additives to enhance, control, or otherwise direct the intended therapeutic effect of the cells comprising said pharmaceutical composition, and/or auxiliary substances or pharmaceutically acceptable substances, such as minor amounts of pH buffering agents, tensioactives, co-solvents, preservatives, etc. Also, for stabilizing the cell suspension, it is possible to add metal chelating agents. The stability of the cells in the liquid medium of the pharmaceutical composition of the invention can be improved by means of adding additional substances, such as, for example, amino acids such as aspartic acid, glutamic acid, etc. Pharmaceutically acceptable substances that can be used in the pharmaceutical composition of the invention are known, in general, by the skilled person in the art and are normally used in the manufacture of cellular compositions. Examples of suitable pharmaceutical vehicles are described in "Remington's Pharmaceutical Sciences" by E. W. Martin. Illustrative, non-limiting, examples of vehicles for the administration of cells contained in a pharmaceutical composition of the invention include, for example, a sterile saline solution (0.9% NaCl), PBS, etc.

Detailed Description of Embodiments

A number of devices have been developed for harvesting and processing cells from adipose tissue, but these devices can suffer from one or more problems which have precluded wide spread adoption. These problems include difficulty of use, and cost. Thus, there is need for alternate approaches in which a population of active cells with increased yield, consistency and/or purity can be prepared rapidly and reliably, and whereby the need for post-extraction manipulation of the cells can be reduced or eliminated. Ideally this cell population would be obtained in a manner that is suitable for their direct placement into a recipient.

Reference will now be made in detail to the presently preferred embodiments of the invention. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims. The present invention may be practiced in conjunction with various cell or tissue separation techniques that are conventionally used in the art, and only so much of the commonly practiced process steps are included herein as are necessary to provide an understanding of the present invention.

System For Extracting And Processing Adipose Tissue

Various embodiments of the present invention are directed to a system 300 for obtaining purified fraction of adipose-derived mesenchymal stem cells in clinical environment and also to compositions, methods, and systems for using stem cells derived from adipose tissue by placing them directly into a recipient along with additives useful to promote, engender, or support a therapeutic, structural, or cosmetic benefit. In various embodiments, the invention provides a system 300 for extracting and processing adipose tissue to generate a therapeutically effective amount of adipose-derived stem cells for re-introduction into a patient, wherein the system is a simple-to-operate, low-cost system suitable for small and mid-size medical clinics of multidisciplinary specialization.

In a preferred embodiment of the invention, illustrated in FIG. 1, a modified centrifuge tube 100, used in conjunction with various accessories known in the art, are comprised in a system or kit that allows for small physician practices as well as surgical centers to employ affordable methods for safe extraction of mesenchymal stem cells (MSCs) from adipose tissue of any patient or donor for use directly in treatment or for cryostorage (banking). The kit is comprised of centrifuge tube 100 and various other components and may be used to carry out secure, sterile, and closed processes for aspiration of small samples of adipose tissue, components for on-site processing and purification of MSC fractions, and components for quality assessment. The kit, including centrifuge tube 100, is generally operable by a laboratory technician or similarly qualified person, following simple method steps that are described in detail below and that may be taught in appropriate training.

Centrifuge tube 100 maintains a closed, sterile fluid/tissue pathway, receiving adipose tissue samples, and providing as an output more or less enriched samples of mesenchymal stem cells, as desired. This is achieved by use of a kit of sterile containers and tubing, which allows for transfer of tissue and fluid elements within a closed pathway. A series of processing reagents (e.g., saline, enzymes, etc.) may also provided in prepackaged form for introduction into centrifuge tube 100 to allow simple control of the addition of reagents, as well as the temperature and timing of processing, thus simplifying process management by operators. In a preferred embodiment, the entire procedure from tissue extraction through processing and placement into the recipient is performed in a single facility (indeed, even within a single room, such as preferably the room of a patient undergoing a procedure that uses MSCs obtained via the invention).

Tube 100 comprises a main body of conventional design and encompassing an inner volume 160, typically available in various sizes from about 10 ml to as much as 500 ml, and adapted to be used in standard centrifuges equipped to use tubes of the conventional geometry shown in FIG. 1 (although any suitable centrifuge tube geometry known in the art and compatible with centrifuges available in the art may be used, according to the invention).

In an embodiment, the kit or system comprises three principal components: (1) a permanent set of equipment, all of which is known in the art: aspiration pump, shaker, centrifuge and mini-incubator; (2) a plurality of single-use disposable equipment items: aspiration needle/cannula, collection bag, syringes, filters, flasks, and centrifuge tubes 100; and (3) various processing solutions/reagents. The components are preferably adapted to cooperate with one another in order to facilitate extraction and processing of adipose tissue to obtain MSCs, while maintaining sterility and simplifying the process. Tube 100 is provided with a cap 150 that is penetrated by several openings 115, 120, 121, and 122, and a separate fitting 110 mounted generally on a top portion of tube 100 near cap 150 (in fact, it should be appreciated by one having ordinary skill in the art that the various fittings, while all affixed to the upper portion of tube 100, may be arranged variously, with some, all, or none of the fittings passing through cap 150, and in fact cap 150 could optionally be omitted in favor of a tube 100 of unitary construction, which may be disposed of after use). Fitting 120 is penetrated by tube 129, which is fitted with a sterile fitting 125 (such as a luer lock), to allow various reagents or other fluids to be introduced via tube 129 without violating sterile conditions within tube 100. Typically, a sterile syringe is used to add fluids to tube 100 via tube 129. Tubes 130 and 131 penetrate through cap 150 at fittings 121 and 122 respectively, and are provided with sterile fittings 126 and 127, so that cells or other materials contained in a pellet at the bottom (the point of the inverted cone that makes up the lower portion of tube 100 after centrifuging (the creation of pellets of matter of relatively higher specific gravity during centrifuging is well known in the art). Fittings 126 and 127 may be of any type, such as a luer lock, known in the art and suitable for establishing a sterile connection between tubes 130, 131 and a syringe or other device capable of applying suction to remove cells from a pellet at the bottom of tube 100. Fitting 115 is penetrated by tube 116, which is fitted with a sterile fitting 117 at its end, and may be used to apply suction from the upper portion of tube 100 to establish a vacuum within tube 100 (for example, to facilitate rapid introduction of lipoaspirate into tube 100 through fitting 110). Fitting 110 is connected via a short tube or stub to fitting 111, which (like all the other fittings passing into tube 100) is suitable to maintaining sterile conditions within tube 100 at all times. Fitting 110 is generally used to inject lipoaspirate into tube 100 as an initial step of a process of extracting and potentially purifying or concentrating MSCs from the lipoaspirate into a pellet that can be withdrawn via either of tubes 130 and 131. In a preferred embodiment, two tubes 131, 131 are provided to ensure that pellet extraction will be possible even if one of the tubes becomes clogged.

Figure 2:
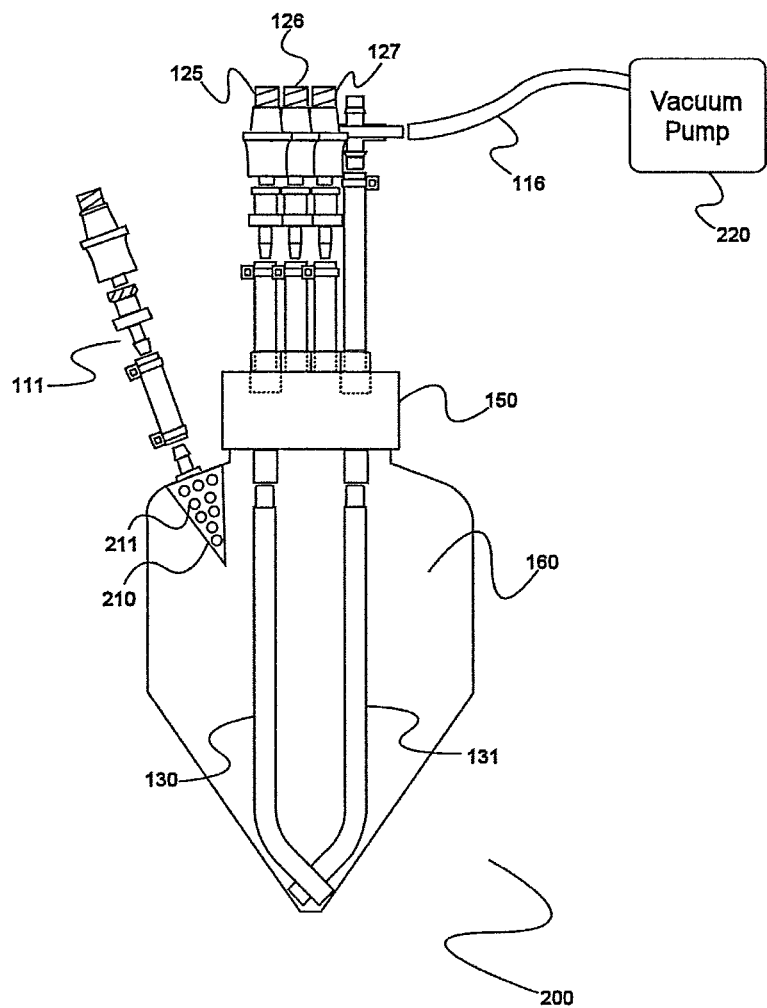
FIG. 2 is a diagram illustrated a modified centrifuge tube for extracting stem cells from adipose tissue that comprises a novel atomization means, according to a preferred embodiment of the invention.

FIG. 2 illustrates illustrated a modified centrifuge tube 200 for extracting stem cells from adipose tissue that comprises a novel atomization means, according to an embodiment of the invention. It will be recognized by one having ordinary skill in the art that tube 200 is very similar to tube 100, but provides more illustrative detail regarding fitting 125-127. Tube 116 also is terminated in a secure way to a vacuum pump 220 (details of the sterile connection between tube 116 and pump 220 are not shown, but are well known in the art). Vacuum pump may be provided, already sterilely connected to tube 116, as a component of a portable kit for MSC isolation from lipoaspirate, or more commonly it may be connected as needed to tube 116 during performance of a process for MSC extraction from a lipoaspirate. In general, it is a goal of the invention to facilitate the rapid breakdown of lipoaspirate as it enters tube 100 into small droplets so that breakdown of adipose tissue and washing of cells (without damaging them) may take place efficiently without requiring special equipment. Thus, in some embodiments, a turbo or screen 210 may be provided, which comprises a plurality of holes 211 through which lipoaspirate must pass when entering tube 100 through fitting 110; the presence of holes 211 helps to break down clumps of adipose tissues that make up at least part of the entering lipoaspirate. It should be noted that lipoaspirate may be drawn into tube 100 using a vacuum provided by pump 220 or another means of drawing suction through tube 116, or by direct injection of lipoaspirate (such as with a plunger-type syringe) through fitting 110. Either way, as lipoaspirate is forced through fitting 110 and then holes 211, it is broken up into small droplets or small clumps of cells and tissue fragments, which are more readily washed and otherwise processed according to methods described elsewhere herein (for example, with reference to FIG. 4).

Figure 3:
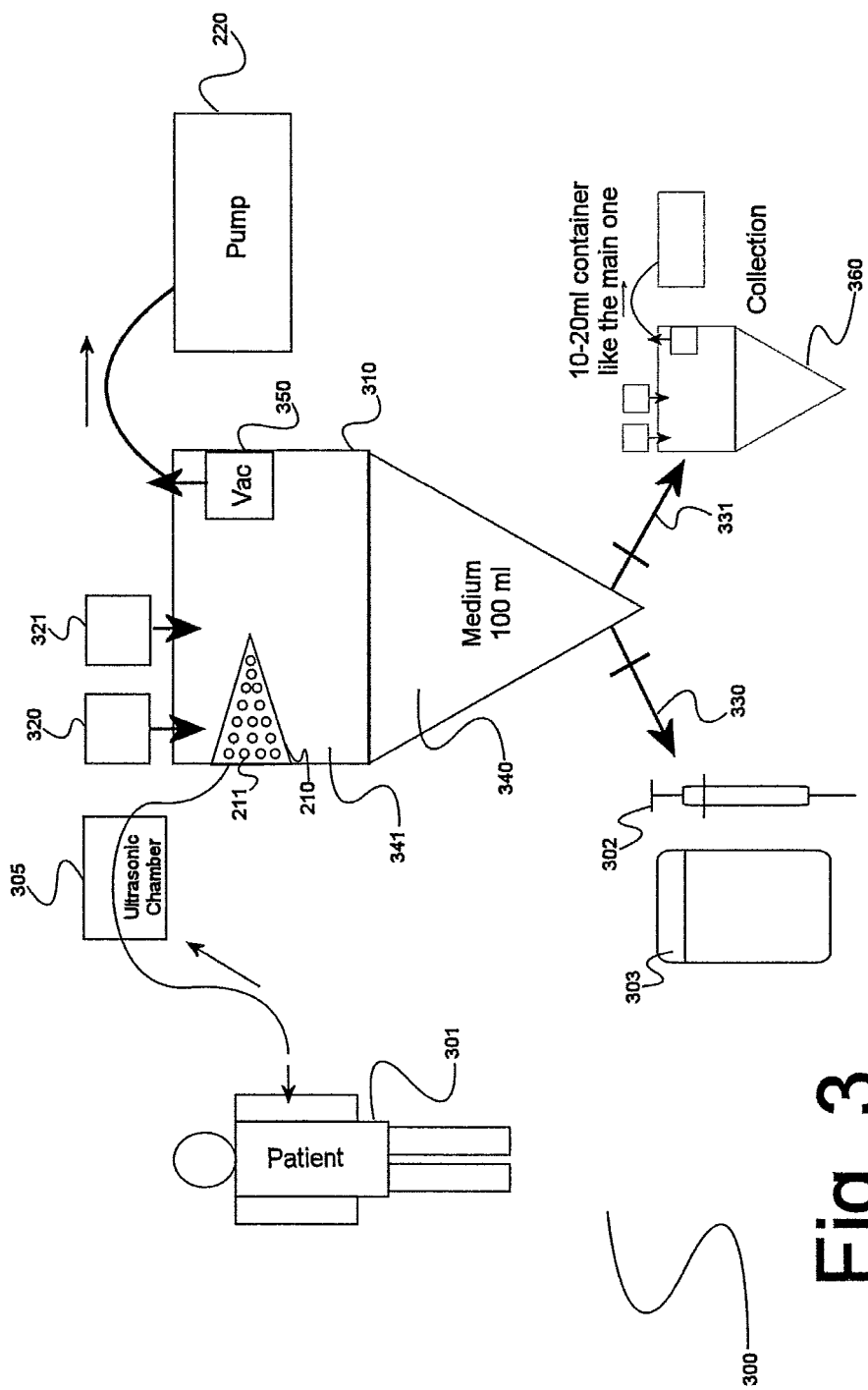
FIG. 3 is a diagram illustrating a system for preparing mesenchymal stem cells from adipose tissue for clinical use, according to a preferred embodiment of the invention.

FIG. 3 is a diagram illustrating a system 300 for preparing mesenchymal stem cells from adipose tissue for clinical use, according to an embodiment of the invention. According to the embodiment, a kit comprising various components, as described above, is provided to allow extraction of adipose tissue from a patient 301 (although a non-patient donor may also provide adipose tissue, according to the embodiment, using system 300). Adipose tissue may, as discussed above, be obtained in a number of ways known in the art. According to an exemplary embodiment, as shown in FIG. 3, system 300 comprises a syringe 302 and a sterile, sealed bag 303 for use in obtaining adipose tissue from patient 301. Syringe 302 may be of any conventional type known in the art that is suitable for use in withdrawing, via manual suction, varying amounts of adipose tissue, typically from 1 to a few hundred milliliters. Various kits according to system 300 may provide one or more means for dissociating adipose tissues, such as ultrasonic chamber 305. Adipose tissue may be placed in ultrasonic chamber 305 while still in sterile bag 303, or it may be passed through ultrasonic chamber 305 via a sterile tube, as shown. System 300 typically comprises at least one medium size (about 100 milliliters) modified centrifuge tube 310 (such as those described above with reference to FIGS. 1 and 2). Adipose tissue may be drawn into tube 310 by application of a vacuum 350 to an inner region 340-341 of tube 310, or by injection from a syringe directly or via a sterile tube. Lipoaspirate is generally admitted via a turbo or screen 210 perforated by a plurality of holes 211, which as described above serves to assist in breaking down incoming adipose tissue samples into small droplets that are more amenable to efficient processing within tube 310. Once a sample of lipoaspirate has been placed inside tube 310, a plurality of washing agents 320 or reagents 321 (for example, reagents that assist in tissue dissociation) may be injected from sterile containers provided as part of a kit of system 300 via one or more sterile fittings (such as those shown in FIGS. 1 and 2, for example fitting 125). As described above, tube 310 is adapted for easy use within a centrifuge (which may be provided as part of a kit of system 300, or which alternatively may be a standard desktop or other centrifuge present in a location where system 300 is to be used; centrifuges are well known in the art and are generally readily available in a wide range of medical facilities), so lipoaspirates in tube 310 may be easily centrifuged in order for example to separate stem cells from other cell or tissue fractions. Tube 310 is generally provided with one or more fittings 330, 331 for removal of separated stem cells or other cells or material contained in a pellet at the apex of conical section 340 of tube 310. Examples of such fittings 330, 331 are shown in FIGS. 1 and 2 (that is, fittings 126 and 127, which draw pelletized material from tubes 130 and 131, respectively). In some embodiments, lipoaspirate treated in tube 310 (by any of washing, dissociating, and centrifuging) is administered directly to patient 301; in other embodiments, system 300 may comprise a second, generally smaller tube 360 that may be used to further process lipoaspirate after its removal from tube 310. For example, a partially enriched lipoaspirate (that is, a processed lipoaspirate with a higher stem cell fraction than was present when the lipoaspirate was initially drawn from patient or donor 301) may be injected (or drawn by vacuum 350) into tube 360, which may be for example of a volume of 10 to 20 milliliters (although other volumes may be used, including the same or a greater volume as that of tube 310; the relative sizes shown and described are merely exemplary and should not be taken as limiting, particularly as various treatment protocols may require different specific tube sizes). Thus system 300 shown in FIG. 3 is exemplary, and shows a variety of apparatus that may be comprised, along with various reagents and washing agents in sterile containers for use as needed, in a kit suitable for use in a single treatment in which lipoaspirate is drawn from a patient 301, processed in a portable, continuous sterile environment comprised of elements of system 300 delivered as a kit, and administered without requiring stem cell culturing or differentiation to the same or another patient 301. It will be appreciated that, in some embodiments, it may be desirable to differentiate a stem cell fraction obtained using system 300 using techniques known in the art, for example to obtain and then culture precursor osteocytes or other precursor cell types differentiable from mesenchymal stem cells obtained according to the invention.

Methods For Extracting And Processing Adipose Tissue

In practicing the methods disclosed herein, cells (such as mesenchymal stem cells) that are intended for administration to a patient 301 may be obtained from adipose tissue. Adipose tissue may be obtained by various methods known to a person of ordinary skill in the art. For example, adipose tissue may be removed from a patient by suction-assisted lipoplasty, ultrasound-assisted lipoplasty, and excisional lipectomy. In addition, the procedures may include a combination of such procedures, such as a combination of excisional lipectomy and suction-assisted lipoplasty. As the tissue or some fraction thereof is intended for reimplantation into a patient the adipose tissue should be collected in a manner that preserves the viability of the cellular component and that minimizes the likelihood of contamination of the tissue with potentially infectious organisms, such as bacteria and/or viruses. Thus, tissue extraction should preferably be performed in a sterile or aseptic manner to minimize contamination.

Figure 4:
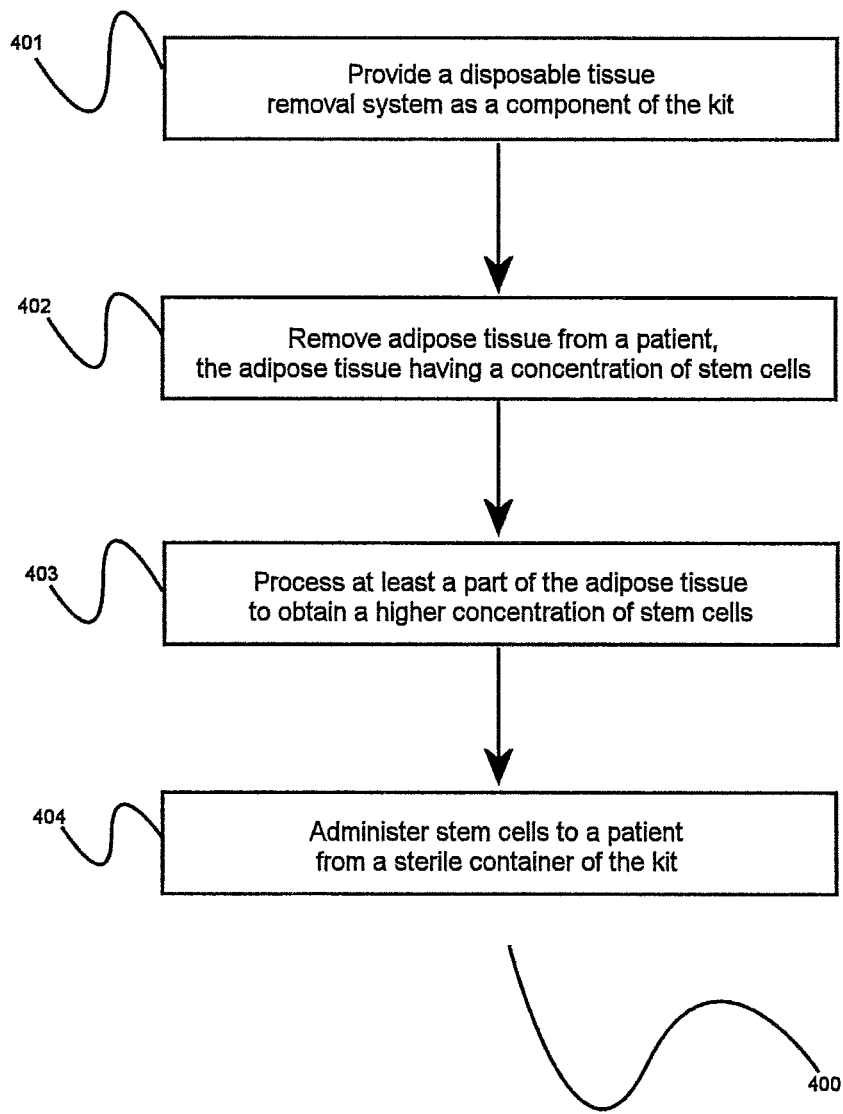
FIG. 4 is a method diagram of a high-level process for preparing mesenchymal stem cells from adipose tissue for clinical use, according to an embodiment of the invention.

FIG. 4 is a method diagram of a high-level process 400 for preparing mesenchymal stem cells from adipose tissue for clinical use, according to an embodiment of the invention. According to the embodiment, in step 401 a disposable tissue removal system is provided as a component of a sterile kit intended for obtaining processed stem cell-rich lip aspirates (for example, a syringe 302). Then, in step 402, a technician, physician, or other professional removes adipose tissue from a patient (or donor), the adipose tissue having an initial concentration of stem cells (particularly MSCs). For suction-assisted lipoplastic procedures, adipose tissue may be collected by insertion of a cannula into or near an adipose tissue deposit present in a patient 301, followed by aspiration of adipose tissue into a suction device. In one embodiment, a small cannula may be coupled to a syringe 302, and adipose tissue may be aspirated using manual force. Using a syringe 302 or other similar device may be desirable to harvest relatively small to moderate amounts of adipose tissue (e.g., from 0.1 ml to several hundred milliliters of adipose tissue).

Suction-assisted lipoplasty may be desirable to remove adipose tissue from a patient 301, as it provides a minimally invasive method of collecting tissue with a correspondingly minimal potential for stem cell damage. Moreover, widespread use of liposuction procedures in the art has led to development of well-established and safe techniques for removal of significant amounts of adipose tissue from donors or patients. In a preferred embodiment, the system includes a single-use disposable aspiration system, which allows extraction of adipose tissue into a sterile sealed bag for further processing. Preferably the system employs a relatively small device such as a small syringe 302, with the concomitant advantage that lipoaspiration may be performed with only local (or even no) anesthesia, as opposed to general anesthesia.

Adipose tissue removed from a patient may be collected into a sterile container (such as sterile sealed bag 303) for further processing. As discussed herein, and in one embodiment, a device is designed for and dedicated to the purpose of collecting tissue for manufacture of a processed adipose tissue cell population, which includes stem cells and/or endothelial precursor cells. In a preferred embodiment, the device is a single-use disposable aspiration system that extracts adipose tissue from a patient into a sterile sealed bag 303. In alternative embodiments, the device may be any conventional device that is typically used for tissue collection by physicians performing the extraction procedure.

Because only small amounts of adipose tissue are typically required, the utility of this invention is not limited to individuals with large amounts of adipose tissue. The amount of tissue to be collected will be dependent on a number of variables including, but not limited to, donor body mass index, availability of accessible adipose tissue harvest sites, concomitant and pre-existing medications and conditions (such as anticoagulant therapy), and the clinical purpose for which adipose tissue is being collected. Moreover, stem cell concentrations present in lipoaspirates vary widely from individual to individual, so that, when a specific amount of stem cells are required, more or less volume of adipose tissue may be required to obtain a specific desired amount. For example, concentration of stem cells in tissue extracted from a lean individual will typically be greater than that extracted from an obese donor (this reflects a typical dilutive effect of increased fat content in adipose tissue in obese individuals).

A preferred method to obtain human adipose tissue is by excision or liposuction procedures well known in the art. Pluripotent cells of the invention are present in an initially excised or extracted adipose tissue, regardless of the method by which the adipose tissue is obtained. Adipose tissue may then be processed to facilitate separation/concentration of stem cells. For example, pluripotent cells may be obtained by washing collected adipose tissue with a physiologically-compatible solution, such as phosphate buffer saline (PBS). Typically, a washing step consists of rinsing a sample of adipose tissue with PBS, agitating the sample, and allowing the tissue in the sample to settle. In addition to washing, adipose tissue may be dissociated. Dissociation may occur by enzyme degradation (e.g., trypsin treatment). Alternatively, or in conjunction with such enzymatic treatment, other dissociation methods may be used, such as mechanical agitation, sonic or ultrasonic energy, or thermal energy. Cells may then be centrifuged, and the resulting pellet (containing pluripotent cells) may be further treated after resuspension in an appropriate solution (e.g., PBS).

In step 403, at least part of the adipose tissue obtained in step 402 is processed (as described above, for example) to obtain a higher concentration of stem cells, and in step 404 the processed stem cells are administered to a patient 301 from a sterile container that may be provided in a kit of system 300 or may be available in a medical facility. Pluripotent cells in a resuspended pellet can be separated from other cells of the resuspended pellet by methods that include, but are not limited to, cell sorting, size fractionation, granularity, density, molecularly, morphologically, and immuno-histologically (e.g., by panning, using magnetic beads, fluorescence-activated cell sorting/FACS, magnetically activated cell sorting/MACS, or affinity chromatography). In some immunologically based methods of cell isolation, a pluripotent cell may be obtained by positive selection, via use of an antibody or other specific-binding protein, which binds to an epitope on the cell surface. In such methods, recovery of cells from antibodies to which they have adhered may be performed by one or more washes with suitable buffers, as is known to one skilled in the art. Alternatively, pluripotent cells may be isolated by negative selection. According to various embodiments of the present invention, stem cell collection kits may comprise sterile containers and/or reagents to facilitate separation or concentration of stem cells in a lipoaspirate sample. The presence of pluripotent cells is preferably assessed prior to reintroduction using, for example, specific cell surface markers and/or counting techniques known in the art.

Pluripotent cells obtained using system 300 of the present invention will typically be introduced (or reintroduced) to a patient without expansion or differentiation. However, in some embodiments, pluripotent cells may be expanded and or differentiated in vitro. That is, after isolation, pluripotent cells may be maintained and allowed to proliferate in a culture medium. Pluripotent cells may be induced to differentiate (or to phenotypically change) into a desired cell type using techniques known in the art. It is within the skill of one in the art to modify or modulate concentrations of media and/or media supplements as necessary for the cells used. In another embodiment, pluripotent cells of the invention may be expanded in a culture medium of definite composition, in which serum is replaced by a combination of serum albumin, serum transferrin, selenium, and recombinant proteins including, but not limited to: insulin, platelet-derived growth factor (PDGF), and basic fibroblast growth factor (bFGF), as known in the art. Maintenance conditions of pluripotent cell population(s) of the invention may also comprise one or more cellular factors that allow cells to remain in an undifferentiated form.

If differentiation of pluripotent cells is desirable, one or more additional substances may be added to a culture to induce a specific desired phenotypic change. Such substances may comprise one or more activators of intracellular signaling pathways (e.g., mitogen-activated protein kinases and SMADs), activators of transcription factors (e.g., sox9, L-sox5, and L-sox6), activators of production and interaction with extracellular matrix proteins (e.g., collagen II, aggrecan, and cartilage oligomeric matrix protein), growth factors, cytokines, chemokines, hormones, and environmental factors (e.g., oxygen tension).

Figure 5:
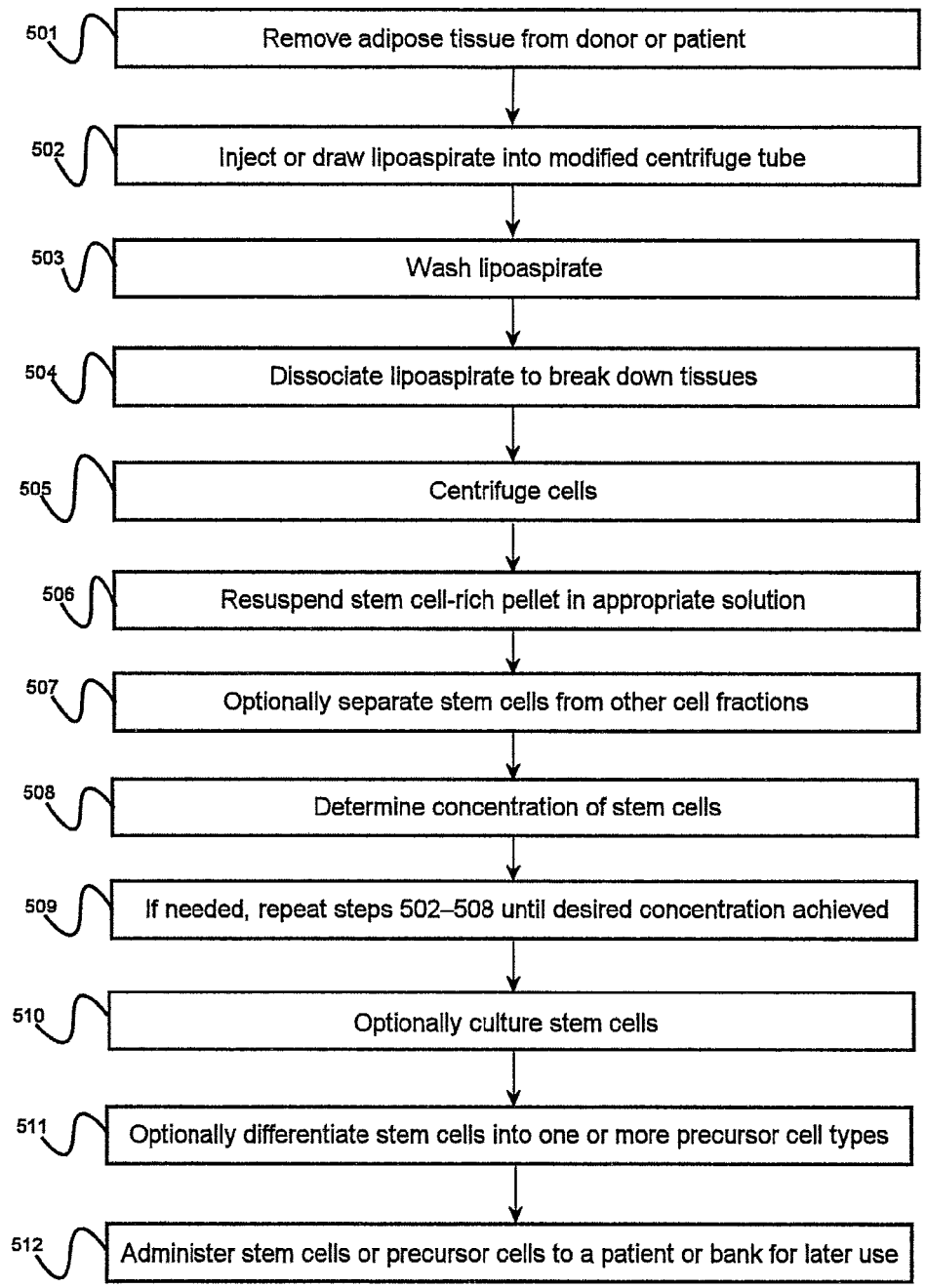
FIG. 5 is a method diagram of a detailed process for preparing and using mesenchymal stem cells from adipose tissue in clinical applications, according to a preferred embodiment of the invention.

FIG. 5 is a method diagram of a detailed process 500 for preparing and using mesenchymal stem cells from adipose tissue in clinical applications, according to a preferred embodiment of the invention. According to the embodiment, in step 501 adipose tissue is removed from a donor or patient 301. In step 502, lipoaspirate is injected or drawn by vacuum 350 in a modified centrifuge tube 310. Optionally, in step 503 the extracted lipoaspirate may be washed using washing agents known in the art, such as PBS. In step 504 lipoaspirate may optionally be dissociated to break down adipose tissues and cell clumps, in order to facilitate subsequent processing. In step 505, the cells or lipoaspirate may be centrifuged to separate cell and tissue fractions with varying specific gravities. For example, in a suitably prepared lipoaspirate, MSCs may be formed into a pellet at the apex of conical volume 340 of tube 310 and thus be isolated to an appreciable extent from lighter cells or tissue fragments. In many cases, a pellet produced as a result of step 505 may have a slightly enriched stem cell concentration (relative to the concentration of stem cells present in lipoaspirate as it was extracted from the donor or patient in step 501), and further enrichment may be desired. In step 506, a stem cell rich pellet may be resuspended in an appropriate solution for further treatment (including potentially repeating of steps 502 through 505). In step 507 stem cells may optionally be further segregated from other cell fractions using techniques known in the art. Pluripotent cells in a resuspended pellet can be separated from other cells of the resuspended pellet by methods that include, but are not limited to, cell sorting, size fractionation, granularity, density, molecularly, morphologically, and immuno-histologically (e.g., by panning, using magnetic beads, fluorescence-activated cell sorting/FACS, magnetically activated cell sorting/MACS, or affinity chromatography). In some immunologically based methods of cell isolation, a pluripotent cell may be obtained by positive selection, via use of an antibody or other specific-binding protein, which binds to an epitope on the cell surface. In such methods, recovery of cells from antibodies to which they have adhered may be performed by one or more washes with suitable buffers, as is known to one skilled in the art. Alternatively, pluripotent cells may be isolated by negative selection. In step 508, the concentration of stem cells in a processed lipoaspirate sample may be determined using any of various means known in the art. The presence of pluripotent cells is preferably assessed prior to reintroduction using, for example, specific cell surface markers and/or counting techniques known in the art. In step 509, a determination may be made, based at least in part on the concentration determined in step 508, as to whether further processing of a lipoaspirate to further concentrate it (that is, to make the concentration of stem cells higher), and if so such further processing may be undertaken through repetition of one or more of steps 502 through 508. In step 510, stem cells may optionally be cultured to obtain a larger quantity of stem cells, using techniques well established in the art. Similarly, in step 511 (which may be performed either before or after, or indeed concurrently with, step 510), pluripotent stem cells may be differentiated into one or more types of precursor cell types using techniques known in the art. Finally, in step 512 stem cells or precursor cells extracted and processed as described above with reference to steps 501 through 511 may be administered to one or more patients 301, or banked for later use in therapeutic, cosmetic, or other applications.

Means for Re-Introducing Adipose-Derived Stem Cells

Kits according to system 300 of the present invention may be used to generate a pharmaceutical composition that contains a prophylactically or therapeutically effective amount of mesenchymal stem cells of the invention, preferably in a substantially purified form, together with a suitable vehicle in appropriate amounts, in order to provide stem cells in a form suitable for safe and efficacious administration to a patient.

Patients undergoing treatment in accordance with various embodiments of the invention may receive different concentrations of stem cells than other treatments employing adipose tissue or stem cells derived from adipose tissue. Thus, adipose tissue that is removed from a patient may be processed to change the concentration of stem cells that are administered to a patient. In a preferred embodiment of the invention, patients receive a higher concentration of stem cells than the concentration of stem cells typically present in adipose tissue transplants and other similar stem cell based therapies. The concentrated stem cells may be administered in a composition comprising adipose-derived stem cells and/or endothelial precursor cells substantially free from mature adipocytes and connective tissue, or, as another example, the concentrated stem cells may be administered in a composition comprising a unit of adipose tissue with an increased amount of stem cells.

The pharmaceutical composition of the invention may be formulated according to a specific chosen form of administration. For example, a pharmaceutical composition may be prepared in a liquid dosage form, e.g., as a suspension, to be injected into a subject in need of treatment. Illustrative (non-limiting) examples include formulating the pharmaceutical composition of the invention in a sterile suspension with a pharmaceutically acceptable vehicle, such as saline solution, phosphate buffered saline solution (PBS), or any other suitable pharmaceutically acceptable carrier, for administration to a subject, e.g., a human being, preferably via intravenous, intraperitoneal, subcutaneous, etc., although further administration routes may be also possible.

The administration of a pharmaceutical composition to a subject in need thereof can be carried out by conventional means, according to the invention. In a particular embodiment, a pharmaceutical composition may be administered to a subject in need by intravenous administration using devices such as syringes, catheters, trocars, cannulas, etc. In any case, a pharmaceutical composition of the invention may be administered using any appropriate equipment, apparatus, and devices known to persons having ordinary skill in the art. In preferred embodiments, a device for administering a pharmaceutical composition is provided as part of a kit described above, or is adapted for use with a kit described above to facilitate transfer of a pharmaceutical composition to a subject without contamination.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

The skilled person will be aware of a range of possible modifications of the various embodiments described above. Accordingly, the present invention is defined by the claims and their equivalents.

What is claimed is:

1. A tissue processing device comprising:
a first centrifuge tube configured to receive and process a biological substance, the first centrifuge tube comprising a sterile tissue inlet fitting, at least one sterile processing fluid inlet fitting, a sterile suction fitting, and at least one sterile extraction port connected to a first extraction tube; and
a second centrifuge tube configured to receive and further process the biological substance from the first centrifuge tube, the second centrifuge tube comprising at least one sterile processing fluid inlet fitting, a sterile suction fitting, and at least one sterile extraction port connected to a second extraction tube, wherein the second centrifuge tube is releasably connected via the at least one sterile processing fluid inlet fitting to one of the at least one sterile extraction ports of the first centrifuge tube.

2. A method for preparation of adipose-derived stem cells, the method comprising the steps of:
(a) performing a sterile transfer of lipoaspirate to the first centrifuge tube of the device claimed in claim 1;
(b) processing the lipoaspirate in the first centrifuge tube by adding one or more fluids via the at least one fluid inlet fitting, the processing comprising one or more of cleaning and dissociating the lipoaspirate;
(c) centrifuging the first centrifuge tube containing processed lipoaspirate to concentrate a pellet comprising an enriched stem cell fraction;
(d) performing a sterile transfer of the concentrated pellet comprising an enriched stem cell fraction to the second centrifuge tube of the device claimed in claim 1;
(e) washing the cell fraction in the second centrifuge tube by adding one or more fluids via the at least one fluid inlet fitting;
(f) centrifuging the second centrifuge tube containing cell fraction to concentrate a pellet comprising an enriched stem cell fraction;
(g) resuspending the pellet in a fluid to obtain a cell mixture substantially enriched in stem cells relative to a concentration of stem cells of the original lipoaspirate; and
(h) administering the resuspended cell mixture to a human being for a therapeutic or cosmetic purpose.

3. The system of claim 1, wherein the first centrifuge tube has a top and an apex wherein the sterile inlet fitting, the at least one sterile processing fluid inlet fitting, the sterile suction fitting, and the at least one sterile extraction port are located adjacent the top of the first centrifuge tube.

4. The system of claim 1 wherein the first and second extraction tubes extend a distance within the first centrifuge tube from the extraction port towards the apex.

5. The system of claim 3 wherein the at least one sterile processing fluid inlet fitting, the sterile suction fitting, and the at least one sterile extraction port are disposed within a cap that affixes the top of the first centrifuge tube.

6. The system of claim 1 further including a vacuum device affixed to the suction fitting.

7. A system for processing tissue in a closed pathway for maintaining sterility comprising:
a first centrifuge tube having an essentially cylindrical body having a top, an inverse conical apex and an interior volume, the first centrifuge tube further comprising:
a tissue inlet fitting,
a suction fitting,
at least one processing material inlet fitting,
at least two extraction fittings;
an extraction tube releasably affixed to each of the at least two extraction fittings that extends a distance within the interior volume towards the apex; and
a screen disposed within the interior volume of the body; and, a second centrifuge tube comprising an essentially cylindrical body having a top, an inverse conical apex, and an interior volume, the second centrifuge tube further comprising a tissue inlet fitting, a suction fitting, an extraction fitting, and an extraction tube releasably affixed to the extraction fitting that extends a distance within the interior volume towards the apex, wherein the second centrifuge tube is releasably connected via the tissue inlet fitting to one of the at least two extraction fittings of the first centrifuge tube.

8. The system of claim 7 wherein the screen divides the interior volume of the first centrifuge tube into an upper portion and a lower portion, and further wherein the screen is adapted to disassociate the tissue in said lower portion.

9. The system of claim 7 further comprising a vacuum device connected to the suction fitting for drawing tissue into the interior volume.

10. The system of claim 7 wherein the tissue inlet fitting, suction fitting, at least one processing material inlet fitting, and at least two extraction fittings are located adjacent the top of the first centrifuge tube.

11. The system of claim 7 wherein the extraction tubes variably extend a distance within the first centrifuge tube from the at least two extraction fittings towards the apex.

12. The system of claim 10 wherein the at least one processing material inlet fitting, suction fitting, and at least one sterile extraction fitting are disposed within a cap that affixes the top of the first centrifuge tube.

13. A multiple unit enabled system for processing tissue in a closed pathway for maintaining sterility comprising:
a centrifuge tube having an essentially cylindrical body having a top, an inverse conical apex and an interior volume and further comprising:
a tissue inlet fitting,
a suction fitting,
at least one processing material inlet fitting,
at least two extraction fittings,
an extraction tube releasably affixed to each of the at least two extraction fittings that extends a distance within the interior volume towards the apex, and
a screen disposed within the interior volume of the body; and,
a container having an inlet fitting, at least one extraction fitting, and a suction fitting wherein the inlet port can be releasably connected to one of the at least two extraction fittings of the centrifuge tube for the sterile transfer of material contained with the closed system.

14. The system of claim 13 further comprising a vacuum device connected to the suction port of the centrifuge tube for drawing tissue into the interior volume.

15. The system of claim 13 wherein the container comprises a second centrifuge tube.

16. The system of claim 13, the container further including a vacuum device connected to the suction fitting of the container for drawing tissue from the centrifuge tube into the container.

17. The system of claim 7 further comprising a syringe connected to the suction fitting for drawing tissue into the interior volume.

* * * * *